United States Patent [19]

Brana et al.

[11] Patent Number: 4,874,863

[45] Date of Patent: Oct. 17, 1989

[54] BISNAPHTHALIMIDES

[75] Inventors: Miguel F. Braña; José M. C. Berlanga, both of Madrid, Spain; Gerhard Keilhauer, Dannstadt-Schauernheim; Erich Schlick, Neuhofen, both of Fed. Rep. of Germany

[73] Assignee: Knoll AG, Ludwigshafen, Fed. Rep. of Germany

[21] Appl. No.: 162,490

[22] Filed: Mar. 1, 1988

[30] Foreign Application Priority Data

Mar. 10, 1987 [DE] Fed. Rep. of Germany ....... 3707651

[51] Int. Cl.$^4$ .......................................... C07D 221/14
[52] U.S. Cl. ...................................... 540/99; 547/361; 546/100
[58] Field of Search .................. 544/361; 546/99, 100; 514/253, 296

[56] References Cited

U.S. PATENT DOCUMENTS 4,146,720  3/1979  Roldan et al. .................. 546/99
4,204,063  5/1980  Brana et al. .................... 546/99

Primary Examiner—Richard A. Schwartz
Attorney, Agent, or Firm—Keil & Weinkauf

[57] ABSTRACT

Bisnaphthalimides of the formula I

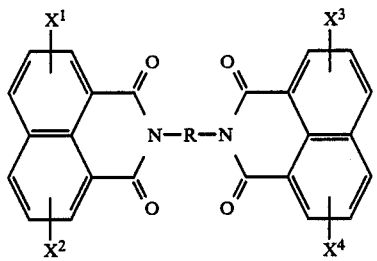

where $X^1$ to $X^4$ and R have the meanings stated in the description, and their preparation are described. The compounds are cytotoxic towards human cells in vitro.

4 Claims, No Drawings

BISNAPHTHALIMIDES

The present invention relates to novel bisnaphthalimides, a process for their preparation and their use in the treatment of disorders.

It is known that certain benzo[de]isoquinolines have tumor-inhibiting properties (Arzneim. Forsch./Drug Research 34 (II) (1984), 1243). However, the actions of these compounds are not satisfactory in every respect.

We have found that bisnaphthalimides of the formula I

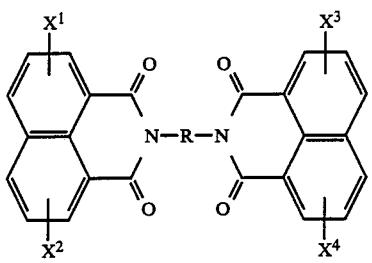

where $X^1$, $X^2$, $X^3$ and $X^4$ are identical or different and are each hydrogen, nitro, amino, $C_1$-$C_6$-alkylamino, di-$C_1$-$C_6$-alkylamino, hydroxyl, $C_1$-$C_6$-alkoxy, halogen, trihalomethyl, $C_1$-$C_6$-alkyl, formyl, $C_1$-$C_6$-alkylcarbonyl, $C_1$-$C_6$-acylamino, ureyl, $C_1$-$C_6$-alkylureyl or $C_1$-$C_6$-alkylcarbonylamino and R is a straight-chain or branched alkylene radical which is interrupted by one or more nitrogen atoms, and where 2 nitrogen atoms may additionally be bonded to one another by an alkylene group, and their salts with physiologically tolerated acids have a better action or a better action spectrum as tumor-inhibiting substances and possess antileukemic activity.

Preferred compounds are those in which $X^1$ and $X^3$ are each amino, acetylamino or nitro and $X^2$ and $X^4$ are each hydrogen, amino, acetylamino or nitro. Among these compounds, particularly noteworthy ones are those in which $X^1$ and $X^3$ are each amino and acetylamino and $X^2$ and $X^3$ are each nitro.

Suitable physiologically tolerated acids for salt formation are organic and inorganic acids, such as hydrochloric acid, sulfuric acid, phosphoric acid, acetic acid, citric acid, oxalic acid, malonic acid, salicylic acid, maleic acid, fumaric acid, succinic acid, ascorbic acid, malic acid, methanesulfonic acid, isethionic acid, lactic acid, gluconic acid, glucuronic acid, amidosulfuric acid, benzoic acid, tartaric acid and pamoaic acid.

The novel compounds can be in the solvated form. Such forms can form, for example, with water or ethanol.

The novel compounds are prepared by reacting a 1,8-naphthalic anhydride of the formula II

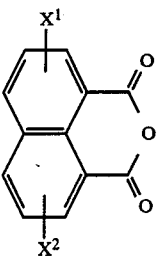

where $X^1$ and $X^2$ have the stated meanings, and a 1,8-naphthalic anhydride of the formula III

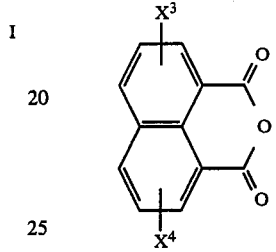

where $X^3$ and $X^4$ have the stated meanings, with an amine of the formula IV

$$H_2N-R-NH_2 \quad\quad IV$$

where R has the stated meanings, and, if required, converting the resulting compound to its salts with physiologically tolerated acids.

The reaction is carried out in a suitable solvent, such as dimethylformamide, methanol, ethanol or propanol, as a rule at room temperature. The novel compound is precipitated from the reaction mixture and can be purified by chromatography and/or recrystallization.

The compounds thus obtained can be converted to their salts in a conventional manner, for example by reaction with an acid.

The novel compounds have a good cytotoxic action, as can be shown in the following experiment. Tumor cells of human origin are plated out on microtiter plates in a concentration of $1-5 \times 10^3$ cells per well and preincubated overnight in a whole medium in an incubator at 37° C. and under a standard atmosphere saturated with water vapor, but with the addition of 5% of carbon dioxide. The substances to be tested are dissolved in the same whole medium, and dilution series (dilution ratio 1:2) are prepared from the solutions. 0.1 ml of each of the solutions thus obtained is introduced into the wells of the microtiter plates. The plates are incubated again for 72 hours at 37° C. Thereafter, adherent cells are stained with crystal violet and nonadherent cells with MTT (tetrazolium), and their absorbance at 540 nm is measured. The decrease in absorbance compared with a blank value (obtained without the test substance) is a measure of the cytotoxicity of the compounds.

EXAMPLE 1

A solution of 2.62 g (0.02 mole) of 3,3-diaminodi(n-propyl)amine in 50 ml of dimethylformamide (DMF) was added dropwise to 9.8 g (0.04 mole) of 3-nitro-1,8-naphthalic anhydride in 100 ml of DMF. The mixture was stirred for 3 hours at room temperature. The precipitated product was filtered off and recrystallized from DMF. 3,3-bis(3-nitro-1,8-naphthalimido)di(n-propyl)amine of melting point 215°–217° C. was obtained in a yield of 65%.

The following were prepared similarly to Example 1:

2. Methyl-3,3-bis(3-nitro-1,8-naphthalimido)di(n-propyl)amine, mp. 207° C. (DMF), yield 76%.
3. 2-(3-nitro-1,8-naphthalimido)ethyl[3-(3-nitro-1,8-naphthalimido)-n-propyl]amine, mp. 237° C. (DMF), yield 72%.
4. 2,2'-bis(3-nitro-1,8-naphthalimido)diethylamine, mp. 235°–237° C., yield 68%.
5. 2-(3-amino-1,8-naphthalimido)ethyl[3-(3-amino-1,8-naphthalimido)-n-propyl]amine, mp. 280° C. (DMF), yield 56%.
6. 3,3'-bis(4-nitro-1,8-naphthalimido)di(n-propyl)amine, mp. 205° C. (DMF), yield 51%.
7. 1,4-bis[3-(3-nitro-1,8-naphthalimido)-n-propyl]piperazine, mp. 246° C. (DMF), yield 55%.
8. 1,4-bis[3-(3-amino-1,8-naphthalimido)-n-propyl]piperazine, mp. 313° C. (DMF), yield 48%.
9. 3,3'-bis(3,6-dinitro-1,8-naphthalimido)di(n-propyl)amine, mp. 350° C. (DMF), yield 42%.
10. 2,2'-bis(3-amino-1,8-naphthalimido)diethylamine, mp. 272° C. (DMF/water), yield 57%.
11. N,N'-bis[3-(3-amino-1,8-naphthalimido-n-propyl]-1,4-diaminobutane, mp. 192° C. (xylenol), yield 45%.
12. N,N'-bis[3-(3-amino-1,8-naphthalimido)-n-propyl]ethylenediamine, mp. 220° C. (DMF), yield 68%.
13. 3,3'-bis(3-amino-1,8-naphthalimido)di(n-propyl)amine, mp. 265° C. (DMF), yield 42%.
14. Methyl-2,2'-bis(3-nitro-1,8-naphthalimido)diethylamine, mp. 261° C. (DMF), yield 56%.
15. Methyl-[2-(3-nitro-1,8-naphthalimido)ethyl]-[3-(3-nitro-1,8-naphthalimido)-n-propyl]amine, mp. 205° C. (DMF), yield 62%.
16. Methyl-3,3'-bis(3-amino-1,8-naphthalimido)di(n-propyl)amine, mp. 201° C. (xylenol), yield 48%.

We claim:

1. A bisnaphthalimide of the formula

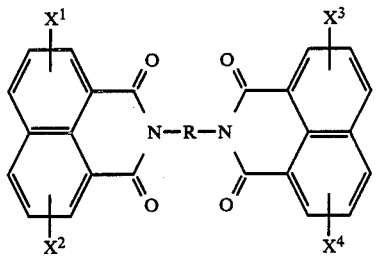

where $X^1$, $X^2$, $X^3$ and $X^4$ are identical or different and are each hydrogen, nitro, amino, $C_1$–$C_6$-alkylamino, di-$C_1$–$C_6$-alkylamino, hydroxyl, $C_1$–$C_6$-alkoxy, halogen, trihalomethyl, $C_1$–$C_6$-alkyl, formyl, $C_1$–$C_6$-alkylcarbonyl, ureyl, $C_1$–$C_6$-alkylureyl or $C_1$–$C_6$ alkylcarbonylamino and R is a straight chain or branched $C_4$–$C_{10}$-alkylene which is interrupted at one or two points in the chain by a secondary or tertiary amino group, where 2 nitrogen atoms may additionally be bonded to one another by an alkylene group, or a salt with a physiologically tolerated acid.

2. The bisnaphthalimide of claim 1 where $X^1$ and $X^3$ are nitro or amino, $X^2$ and $X^4$ are hydrogen and R is alkylene of 4 to 10 carbon atoms interrupted at one or two points of the chain by an amino of methylamino group.

3. 3,3-bis(3-nitro-1,8-naphthalimido)di(n-propyl)amine.

4. Methyl-3,3-bis(3-nitro-1,8-naphthalimido)di(n-propyl)amine.

UNITED STATES PATENT AND TRADEMARK OFFICE
CERTIFICATE OF CORRECTION

PATENT NO. : 4,874,863

DATED : October 17, 1989

INVENTOR(S) : Miguel Fernandez BRANA et al.

It is certified that error appears in the above-identified patent and that said Letters Patent is hereby corrected as shown below:

ON THE TITLE PAGE
IN THE ABSTRACT

The last line should read:

"compounds are cytotoxic towards human tumor cells in vitro."

Signed and Sealed this

Fourth Day of September, 1990

Attest:

HARRY F. MANBECK, JR.

*Attesting Officer*  *Commissioner of Patents and Trademarks*